United States Patent
Zhang et al.

(10) Patent No.: US 12,103,173 B2
(45) Date of Patent: Oct. 1, 2024

(54) SYSTEMS AND METHODS FOR IN VIVO MULTI-MATERIAL BIOPRINTING

(71) Applicant: THE BRIGHAM AND WOMEN'S HOSPITAL, INC., Boston, MA (US)

(72) Inventors: Yu Shrike Zhang, Boston, MA (US); Ali Khademhosseini, Boston, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 1216 days.

(21) Appl. No.: 16/091,193

(22) PCT Filed: Apr. 20, 2017

(86) PCT No.: PCT/US2017/028569
§ 371 (c)(1),
(2) Date: Oct. 4, 2018

(87) PCT Pub. No.: WO2017/184839
PCT Pub. Date: Oct. 26, 2017

(65) Prior Publication Data
US 2020/0324469 A1    Oct. 15, 2020

Related U.S. Application Data

(60) Provisional application No. 62/325,228, filed on Apr. 20, 2016, provisional application No. 62/325,252, filed on Apr. 20, 2016.

(51) Int. Cl.
*B25J 9/04* (2006.01)
*A61L 27/36* (2006.01)
(Continued)

(52) U.S. Cl.
CPC .............. *B25J 9/045* (2013.01); *A61L 27/36* (2013.01); *B25J 9/023* (2013.01); *B25J 9/16* (2013.01);
(Continued)

(58) Field of Classification Search
CPC .... B25J 9/045; B25J 9/023; B25J 9/16; A61L 27/36; B29C 64/141; B29C 64/209;
(Continued)

(56) References Cited

U.S. PATENT DOCUMENTS

2006/0069346 A1    3/2006  Smith et al.
2012/0058174 A1 *  3/2012  West ...................... A61L 27/38
                                                        424/443
(Continued)

FOREIGN PATENT DOCUMENTS

CN    104827672 B      3/2017
JP    2006274370 A  * 10/2006
WO    2015/066705 A1   5/2015

OTHER PUBLICATIONS

International Search Report for Application No. PCT/US17/28569 dated Sep. 5, 2017.
(Continued)

*Primary Examiner* — Thomas C Lee
*Assistant Examiner* — Anzuman Sharmin
(74) *Attorney, Agent, or Firm* — Tarolli, Sundheim, Covell & Tummino LLP

(57) ABSTRACT

Described are systems and methods for in vivo multi-material bioprinting. The in vivo multi-material bioprinting can be used to fabricate biomedical constructs within a patient minimally invasively. The systems and methods can utilize a multi-material bioprinter, which includes a biocompatible portion. The biocompatible portion can include a single printhead for in vivo bioprinting. The single printhead can include a plurality of outlets, each linked to one of a plurality of reservoirs. Each of the plurality of reservoirs can each house a different bioink for bioprinting. Each of the plurality of outlets can be activated to release a respective bioink.

11 Claims, 16 Drawing Sheets

(51) Int. Cl.
  *B25J 9/02* (2006.01)
  *B25J 9/16* (2006.01)
  *B29C 64/141* (2017.01)
  *B29C 64/209* (2017.01)
  *B29C 64/379* (2017.01)
  *B33Y 10/00* (2015.01)
  *B33Y 30/00* (2015.01)
  *B33Y 70/00* (2020.01)
  *B33Y 80/00* (2015.01)

(52) U.S. Cl.
  CPC .......... *B29C 64/141* (2017.08); *B29C 64/209* (2017.08); *B29C 64/379* (2017.08); *B33Y 70/00* (2014.12); *B33Y 10/00* (2014.12); *B33Y 30/00* (2014.12); *B33Y 80/00* (2014.12)

(58) Field of Classification Search
  CPC ..... B29C 64/379; B29C 64/106; B33Y 10/00; B33Y 30/00; B33Y 70/00; B33Y 80/00; C12M 33/00
  See application file for complete search history.

(56) References Cited

U.S. PATENT DOCUMENTS

| | | | | |
|---|---|---|---|---|
| 2012/0089238 A1* | 4/2012 | Kang | | A61L 27/20 623/23.72 |
| 2014/0093932 A1* | 4/2014 | Murphy | | B33Y 30/00 435/177 |
| 2015/0351896 A1* | 12/2015 | D'Lima | | A61F 2/022 604/522 |
| 2016/0046832 A1* | 2/2016 | Wroblesky | | A61L 27/222 425/375 |
| 2016/0054310 A1 | 2/2016 | Brennan et al. | | |
| 2016/0271379 A1* | 9/2016 | Pouliot | | A61B 6/037 |
| 2016/0288414 A1* | 10/2016 | Ozbolat | | C12M 21/08 |
| 2016/0303833 A1* | 10/2016 | Wang | | B32B 5/18 |
| 2017/0157828 A1* | 6/2017 | Mandel | | B29C 48/21 |
| 2018/0290384 A1* | 10/2018 | Hyde | | B33Y 40/10 |
| 2019/0090801 A1* | 3/2019 | Rogers | | A61B 5/4836 |

OTHER PUBLICATIONS

Loz Blain, '3D Bioprinting of Stem Cell Structures Could Combat Osteoarthritis' Apr. 28, 2014, retrieved from the internet on Aug. 23, 2017. URL: <http://newatlas.com/3d-printing-stem-cells-cartilage/31827/>.

* cited by examiner

SYSTEMS AND METHODS FOR IN VIVO MULTI-MATERIAL BIOPRINTING

RELATED APPLICATIONS

The present invention is a U.S. National Stage under 35 USC 371 patent application, claiming priority to Ser. No. PCT/US2017/028569, filed on 20 Apr. 2017; which claims priority of U.S. Provisional Application No. 62/325,228, filed on 20 Apr. 2016, and U.S. Provisional Application No. 62/325,252, filed on 20 Apr. 2016, the entirety of which are incorporated herein by reference.

GOVERNMENT FUNDING

This work was supported, at least in part, by grant numbers R01 AR057837, R01 DE021468, and K99 CA201603 from the United States National Institutes of Health (NIH). The United States government may have certain rights in this invention.

TECHNICAL FIELD

The present disclosure relates generally to multi-material bioprinting and, more particularly, to systems and methods for in vivo multi-material bioprinting.

BACKGROUND

Bioprinting can be used to fabricate biomedical constructs, such as artificial tissues, tissue models, functional biomaterials, biomolecules, biomedical devices, scaffolds, and the like. Recent advances in bioprinting have led to an improved ability to tailor the structural, biological, and/or mechanical properties, which enables fine control of the resulting microarchitecture of the biomedical constructs. However, most current bioprinting technologies are limited to the use of a single bioink at a time, making bioprinting a biomedical construct quite time consuming.

Generally, these biomedical constructs can be fabricated outside the body and implanted into the patient's body thereafter. Implantation of these biomedical constructs generally requires an invasive surgical procedure. Invasive surgical procedures have a high risk of infection and require a long recovery time. Accordingly, there has been a drive to replace invasive surgical procedures with minimally invasive procedures. Minimally invasive procedures use instruments that are inserted into the body through keyhole cuts and tracked within the body using image guidance (e.g., ultrasound, computed tomography, fluoroscopy, or the like). However, it remains impractical to implant the biomedical constructs using a minimally invasive procedure.

SUMMARY

The present disclosure relates generally to multi-material bioprinting and, more particularly, to systems and methods for in vivo multi-material bioprinting. Notably, the systems and methods of the present disclosure can utilize a bioprinter with a single printhead to fabricate biomedical constructs minimally invasively, rapidly, and in vivo.

In one aspect, the present disclosure can include a multi-material bioprinter. The multi-material bioprinter can include a housing that can include a biocompatable portion. The biocompatible portion can include a single printhead for in vivo bioprinting. The single printhead can include a plurality of outlets, each linked to one of a plurality of reservoirs. Each of the plurality of reservoirs can each house a different bioink for bioprinting. Each of the plurality of outlets can be activated to release a respective bioink.

In another aspect, the present disclosure can include a method for multi-material bioprinting. For example, the multi-material bioprinting can be used for in vivo applications. At least one outlet of a plurality of outlets within a printhead of a bioprinter can be activated to print a bioink according to a bioprinting program executed by a controller of the bioprinter. A location of the printhead can be changed in at least one of a rectangular and a spherical coordinate system according to the bioprinting program executed by the controller of the bioprinter. At least one other outlet of the plurality of outlets within the printhead of the bioprinter can be activated to print another bioink according to the bioprinting program executed by the controller of the bioprinter. At least one of the activated outlets within the printhead of the bioprinter can be deactivated to stop printing the associated bioink according to the bioprinting program executed by the controller of the bioprinter.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Figure 1:
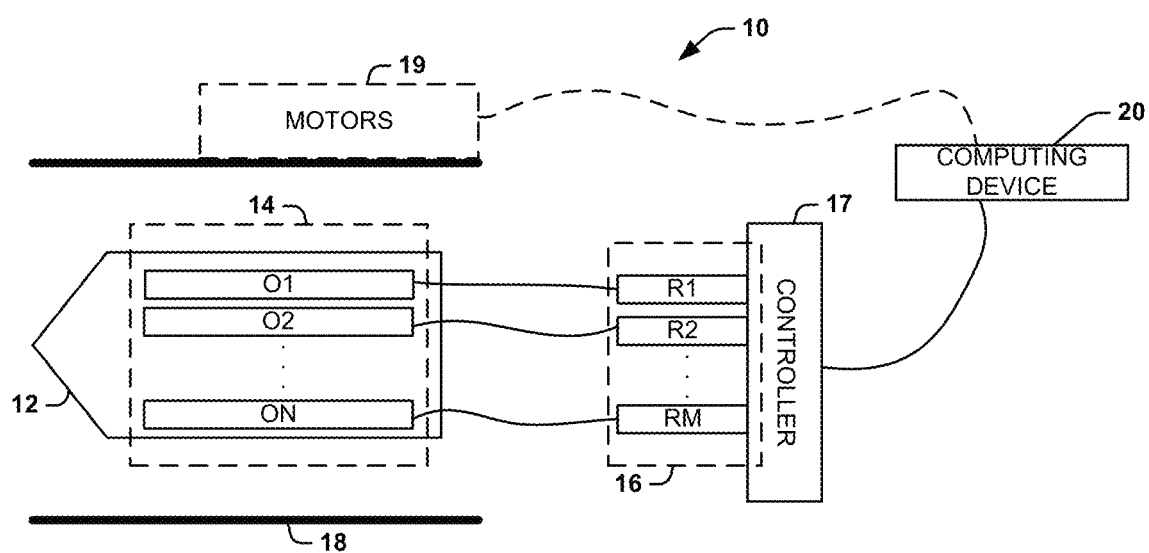
FIG. 1 is a block diagram illustrating an example of a system for in vivo multi-material bioprinting according to an aspect of the present disclosure.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "bioprinting" can refer to a method of biofabrication using a printer to print materials incorporated with living cells or structures that are used for culturing cells or for tissue interactions. Bioprinting can include two-dimensional (2D) bioprinting and three-dimensional (3D) bioprinting. Additionally, bioprinting can refer to extrusion bioprinting or droplet-based bioprinting (like inkjet).

As used herein, the term "2D bioprinting" can refer to a particular means of fabrication of planar biomedical constructs. For example, 2D bioprinting can refer to the deposition of a single layer of microdroplets or material to create a planar biomedical construct.

As used herein, the term "3D bioprinting" can refer to a particular means of fabrication of 3D biomedical constructs. As an example, 3D bioprinting can refer to particularly processes where successive layers or rows of microdroplets or material are deposited under computer control to create the 3D biomedical construct. As an example, a 3D biomedical construct can include a complex biological structure comprising one or more independent three-dimensional constructs.

As used herein, the term "biomedical construct" can refer to a combination of one or more bioprinted materials that incorporate visible living cells. Examples of biomedical constructs include artificial tissues, tissue models, functional biomaterials, biomolecules, biomedical devices (e.g., including multiple components like bioelectronics and high-throughput point-of-care devices), scaffolds, and the like. In some instances, biomedical constructs can be planar 2D structures fabricated via 2D bioprinting. In other instances, biomedical constructs can be 3D structures fabricated via 3D bioprinting.

As used herein, the term "bioprinter" can refer to a 3D printer with one or more printheads coupled to one or more reservoirs that contain different bioinks used for bioprinting biomedical constructs. The bioprinter can be coupled to a computing device (e.g., a controller) to facilitate the construction of the biomedical constructs based on a software model of the biomedical construct. Examples of biomedical constructs that can be fabricated, at least in part, using a bioprinter include artificial tissues, tissue models, functional biomaterials, biomolecules, biomedical devices, scaffolds, and the like.

As used herein, the term "extrusion" when used in connection with bioprinting can include both extrusion (used by an extrusion bioprinter) and ejection (used by an ink jet bioprinter), unless noted otherwise.

As used herein, the term "in vivo" bioprinting can refer to bioprinting that occurs within a patient's body.

As used herein, the term "printhead" can refer to a movable part of the bioprinter that contains printing elements to form at least a portion of the printed biomedical construct.

As used herein, the term "bioink" can refer to a fluid, solid, or hydrogel deposited by a bioprinter. The composition of the bioink can include one or more biological active components, like cells, growth factors, cytokines, anti-infection agents, adhesive molecules, nanoparticles, or the like.

As used herein, the terms "subject" and "patient" can be used interchangeably to refer to any warm-blooded living organism including, but not limited to, a human being, a pig, a rat, a mouse, a dog, a cat, a goat, a sheep, a horse, a monkey, an ape, a rabbit, a cow, etc.

Overview

The present disclosure relates generally to multi-material bioprinting. Bioprinting can be used to fabricate biomedical constructs with a fine control of the resulting microarchitecture. Conventional bioprinting techniques are limited to using a single bioink at a time, suffering from a long transfer time between bioinks. The present disclosure describes a bioprinter configured for multi-material bioprinting. This bioprinter can include a single printhead linked to a plurality of different bioink reservoirs that virtually eliminates the transfer time lag of conventional bioprinters.

In some instances, the multi-material bioprinter can be with a single printhead of the present disclosure can be configured for in vivo use. The in vivo multi-material bioprinting can be used to implant a biomedical construct in a minimally invasive manner. For example, the biomedical construct can be used to treat an infracted heart, one or more joints, a diseased liver, a lung, bone tissue, one or more blood vessels, or one or more cavities in tissue due to abscesses, fistulas, cysts, or surgery. By merging the multi-material bioprinter with a minimally invasive surgical intervention, the need for invasive surgical implantation of biomedical constructs is eliminated. By eliminating the need for invasive surgery, the risk of the patient suffering an infection is reduced and the patient's recovery time is shortened.

Systems

FIG. 1 illustrates a system 10 for multi-material bioprinting in which a plurality of bioinks can be extracted in a continuous manner for rapid fabrication of biomedical constructs. For example, the system 10 can be used for topical or in vivo applications, like aneurism treatment, embolism treatment, wound healing, defect healing, or the like. The system 10 can include a single printhead 12 that can be connected to a plurality of reservoirs (R1-RM, where M is an integer greater than 1) 16. Each of the plurality of reservoirs can include a bioink for bioprinting. In some instances, each of the reservoirs 16 can include a different and unique bioink. In other instances, two or more of the reservoirs 16 can include the same bioink.

The printhead 12 can be connected to the plurality of reservoirs 16 through a plurality of outlets (O1-ON, where N is an integer greater than 1 that is at least equal to M) 14 located within the printhead 12 with fast and smooth switching among different reservoirs. For example, the plurality of outlets 14 may be a plurality of channels bundled within the printhead 12. As another example, the plurality of outlets 14 may be each associated with a valve linked to the respective reservoir 16. Each of the outlets 14 can be loaded with the bioink from the respective reservoir 16.

Each of the outlets 14 can be activated independently based on an extrusion mechanism for extrusion of the bioinks from the respective outlets 14. Examples of the extrusion mechanism can include a mechanical pressure change, a pneumatic pressure change, a thermal activation, a piezo electric activation, and the like. Using the example where each of the plurality of outlets is associated with an individual valve, the respective valve can be configured to open when exposed to a certain extrusion mechanism with a different property for each valve.

One or more of the unique bioinks can be continuously ejected from the respective outlets. As an example, one of the plurality of outlets can be activated by a certain level of the extrusion mechanism, while another of the plurality of outlets can be activated by another level of the extrusion mechanism. The certain level and the other level of the extrusion mechanism can be achieved individually for sequential activation of the outlets and/or simultaneously for simultaneous activation of two or more of the outlets.

The printhead 12, the outlets 14, and/or the reservoirs 16 can be coupled to a controller 17, which includes at least one mechanism to control assembly and adhesion of printed patterns corresponding to biomedical constructs. To this end, the controller 17 can regulate activation and deactivation of the outlets. The activation can cause an outlet to print the bioink therein, while the deactivation can cause the outlet to stop printing. In some instances, like when the bioprinter is a handheld device, the controller 17 can perform the activation and deactivation in response to a signal from a user. In other instances, like where the bioprinter is a robotically controlled device, the controller 17 can communicate with a computing device 20 to receive a signal from the computing device regarding the activation and deactivation. For example, the activation and deactivation can be done according to a preprogrammed set of instructions. In other words, the extrusion of the bioinks can be digitally tuned for a fabrication of a specific biomedical construct. The computing device 20 can also move the single printhead 12 and/or an associated printing stage according to the biomedical construct being printed. In some instances, the computing device 20 can be a separate device located remote from the controller 17. In other instances, the computing device 20 can be part of the controller 17.

As illustrated, the system 10 can be configured for in vivo multi-material bioprinting by enclosing the printhead 12 in a housing 18. For example, the in vivo multi-material bioprinting can provide for programmed delivery of bioinks to specific locations to construct the biomedical construct within the body. The in vivo multi-material bioprinting can be accomplished through self-assembly of the biomedical construct via chemical or physical methods (e.g., DNA-directed, differential swelling, or the like). The in vivo multi-material bioprinting can also be accomplished through the use of motors 19 and a printing program stored on a computing device 20. The use of motors 19 and the printing program will be discussed further herein. The printing program enables programmed, direct in vivo multi-material printing of biomedical constructs.

The housing 18 can include a biocompatible portion for the in vivo bioprinting. The housing can be adapted as a catheter device, a needle device, an endoscopy device, an orthoscopy device, or the like. However, the housing 18 can be any type of device with a biocompatible portion that exhibits a stiffness that is tunable for different applications. The bioprinting can be combined with an optical fiber, in some instances, to perform light delivery, for photocrosslinking of hydrogels, or the like. In some instances, the printhead 12 can be included within the biocompatible portion. For example, the housing 18 can provide a biocompatible shield for the printhead 12.

In some instances, the housing 18 can be configured for motion with one or more motors 19. The motors 19 can be positioned based on movement of the housing 18 in Cartesian coordinates or spherical coordinates. For example, the motors can include one or more of a horizontal-motor, a vertical-motor, and/or a z-motor. The some instances, the motors 19 can be controlled by instructions from the computing device 20. As an example, the housing 18 can be a catheter device. The catheter device can include a movement guide including portions made of rigid poly(methyl methacrylate) (PMMA) and portions made of soft poly(dimethylsiloxane) (PDMS). The movement guide can also include strings or Kevlar wires, which can be connected to one or more motors, to facilitate the automated movement of the catheter device. The catheter device can move with three degrees of freedom (r, θ, φ) in the spherical coordinate system. For example, the rigid PMMA portions, which have the strings or wires therethrough, can be laser cut with a larger inner diameter than the PDMS portions, which are used as spacers. The backbone stiffness of the movement guide can be tunable.

Figure 2:
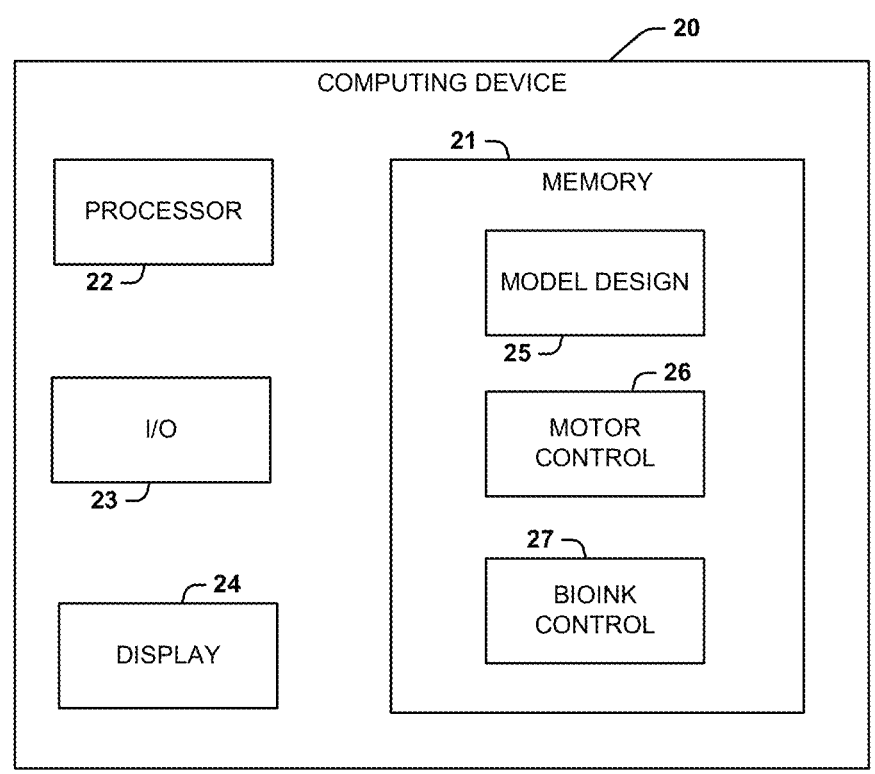
FIG. 2 is a block diagram illustrating an example of a computing device that can be used in connection with the system of FIG. 1.

An example of the computing device 20 is shown in FIG. 2. In some instances, the functionality of the computing device 20 can be embodied in the controller 17. However, in other instances, the computing device 20 can be a standalone device that communicates with the controller 17 and the motors 19. The computing device 20 can include a memory 21 storing data and instructions that are executable by the processor 22. The memory 21 can include any type of non-transitory media (not a transitory signal) that can contain or store data and/or instructions for use by processor 22. Examples (a non-exhaustive list) of non-transitory media can include: an electronic, magnetic, optical, electromagnetic, solid state, infrared, or semiconductor system, apparatus or device. More specific examples (a non-exhaustive list) of non-transitory media can include the following: a portable computer diskette; a random access memory; a read-only memory; an erasable programmable read-only memory (or Flash memory); and a portable compact disc read-only memory. The processor 22 can be any type of device (e.g., a central processing unit, a microprocessor, or the like) that can facilitate the execution of the computer program instructions to perform one or more actions of the computing device 20.

The computing device 20 can also include input/output (I/O) circuitry 23 configured to communicate data with various input and output devices coupled to the computing device 20. For example, the I/O circuitry 23 can receive inputs from a keyboard, mouse, or other peripheral device and provide outputs to and, in some instances, receive inputs from, at least the controller 17 and the motors 19. The computing device 20 can also include a display 24, which can include a graphical user interface (GUI) or other means to display a user-perceivable output and/or receive an input.

The memory 21 of the computing device 20 can include instructions corresponding to a model design 25, motor control 26, and bioink control 27. The model design 25 can relate to the design of a model of a physical biomedical construct that can be printed by the bioprinter. The model can be created in a Cartesian coordinate system, and coordinates of the model can be stored in software code associated with the model and further translated for the printer to print the biomedical construct.

As one example, the model can be created by a user using a software program based on the biomedical construct and stored in the memory 21. For example, the model can correspond to a 3D software model constructed using a computer aided design (CAD) program like SOLID-WORKS® from Dassault Systemes. In another example, the model can be created based on medical imaging data (e.g., 2D or 3D patient imaging data from x-ray, computed tomography (CT), magnetic resonance imaging (MRI), and the like). The medical imaging data can be converted into 3D models; the bioprinter can use at least a portion of the 3D models to print patient-specific structures.

Figure 3:
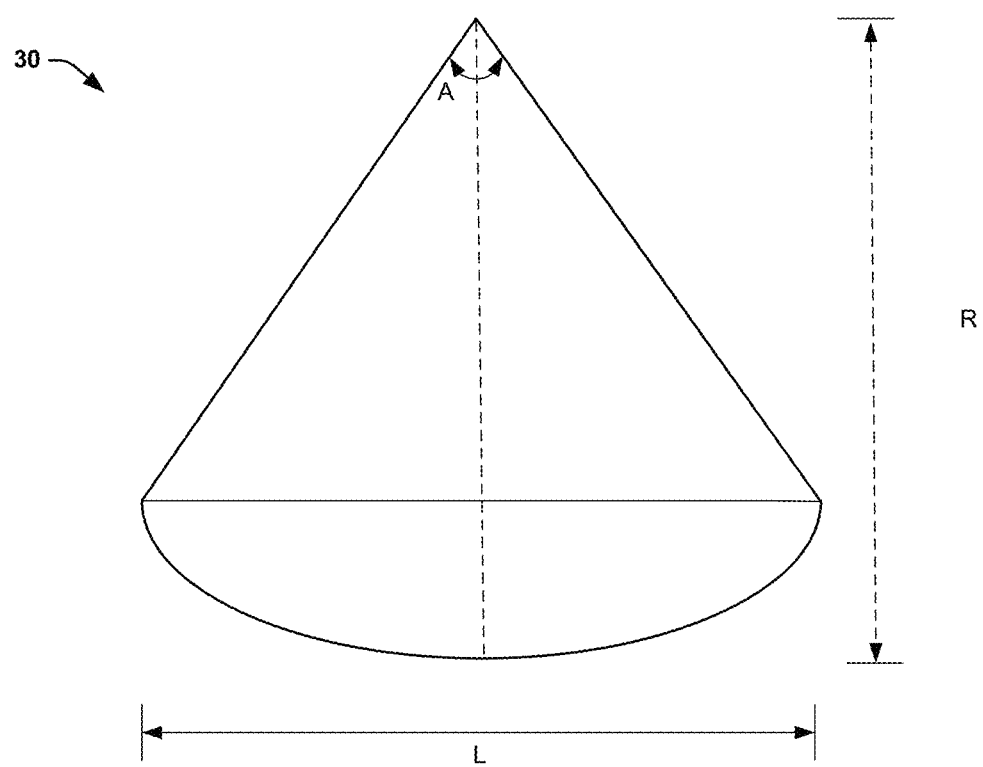
FIG. 3 is an example showing a movement range of the housing of FIG. 1.
Figure 4:
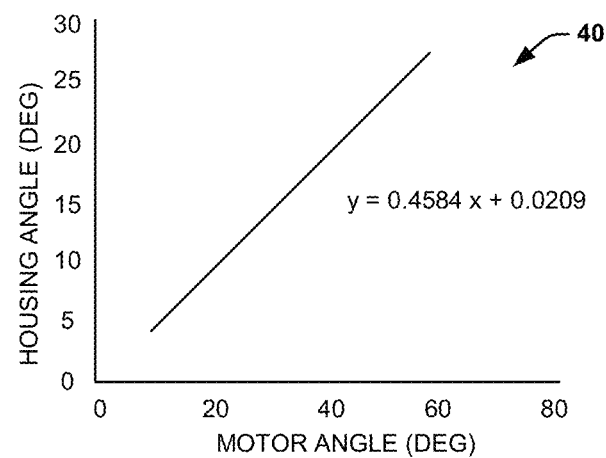
FIGS. 4 and 5 are example plots of motor angle versus the angle of the housing and the resulting chord length.
Figure 5:
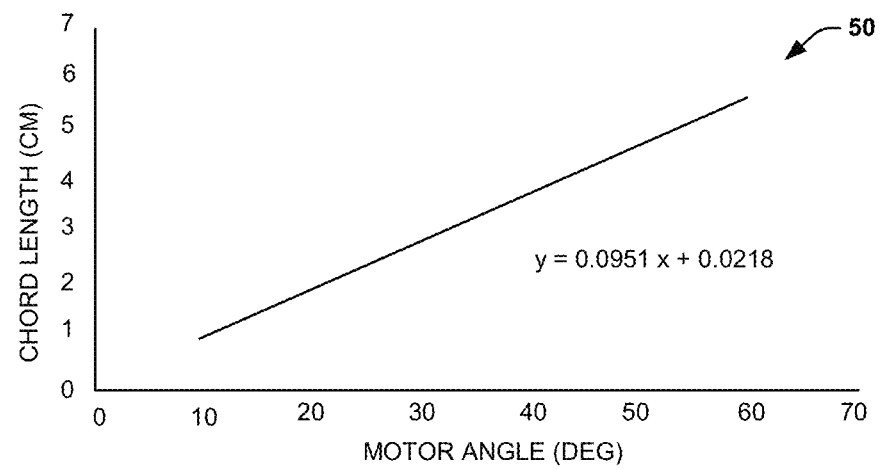

The motor control 26 can control the motors 19 to regulate movement of the housing 18 based on the design of the model of the biomedical construct. For example, the motor control 26 can access the model and process the associated software code associated with the model to translate the Cartesian coordinates to spherical coordinates. However, the motor control 26 can also process the Cartesian coordinates without translating to spherical coordinates. In either case, the motor control 26 can define a maximum and minimum of all three degrees of freedom (either (x. y. z) or (r, θ, φ)), map a range based on the maximums and minimums (e.g., as shown in FIG. 3, the range A=2 asin (L/2R), where L and R are maximum values if the length and the radius), and move one or more of the motors based on the model design. The motors 19 can have a separate controller that can perform at least a portion of the functions of the motor control 26. Additionally, the dependence of the angle of the housing 18 and the chord length on the motor angle is shown in FIG. 5.

The bioink control 27 can regulate the bioprinting process by regulating printing of certain bioinks in a specific manner based on the model of the biomedical construct. For example, the bioink control 27 can regulate activation and deactivation of one or more of the outlets in a time specific manner that correlates with the movement by the motors 19. The regulation can be based on the model of the biomedical construct. Activation of the outlets can be in a pattern that is predefined according to the movement of the motors 19 and/or the model of the biomedical construct. The bioink control 27 can control the specific extrusion parameters to regulate the specific outlets in the pattern.

Methods

Another aspect of the present disclosure can include a method 60 (FIG. 6) for multi-material bioprinting. The multi-material bioprinting can be accomplished, for example, by at least a portion of the system 10 of FIG. 1 (either with the housing 18 or without the housing 18). FIG. 7 shows a method 70 for controlling the multi-material bioprinting. For example, the method 70 can be executed by one or more controllers 17 and/or the computing device 20.

Figure 6:
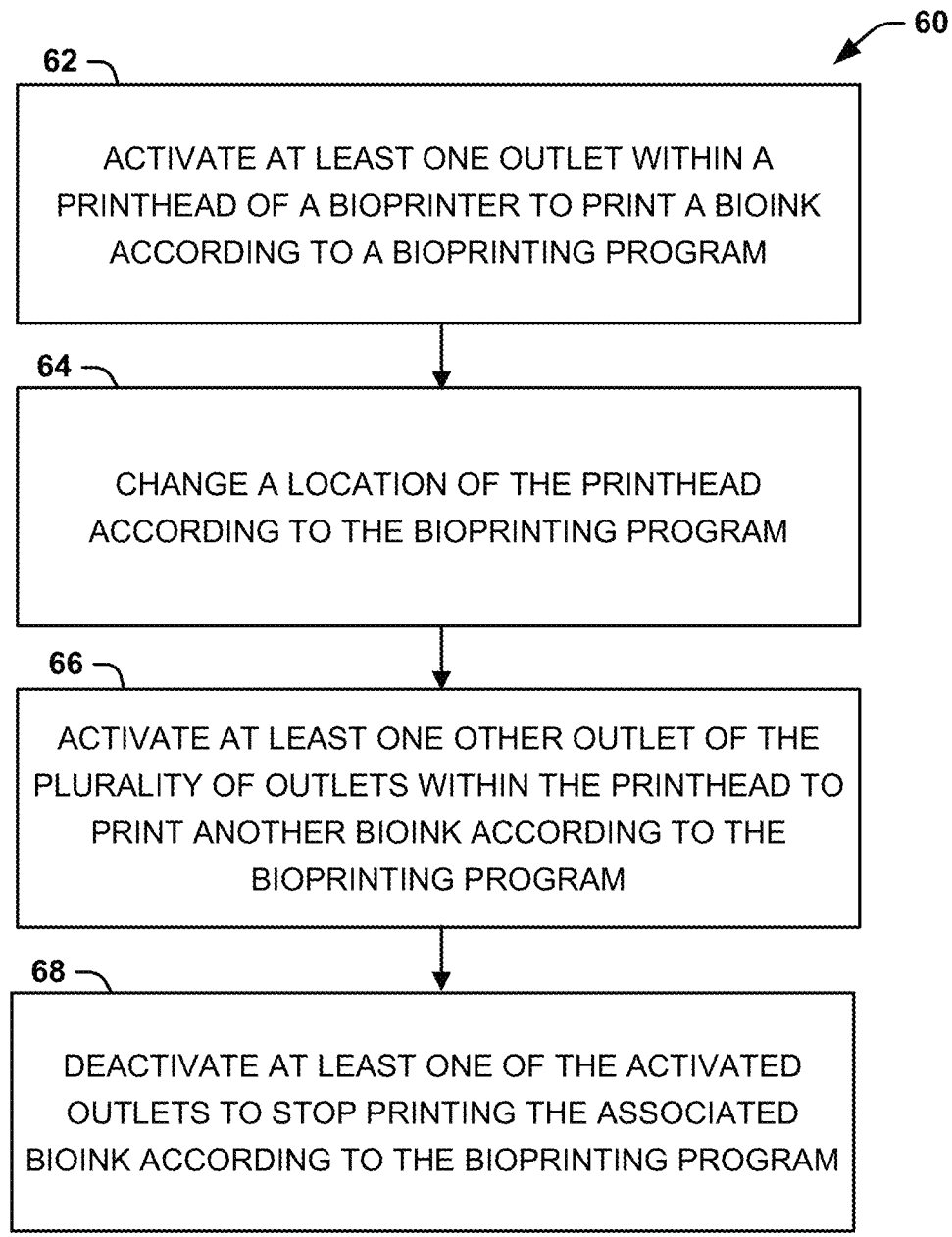
FIG. 6 is a process flow diagram of an example method for multi-material bioprinting according to another aspect of the present disclosure.
Figure 7:
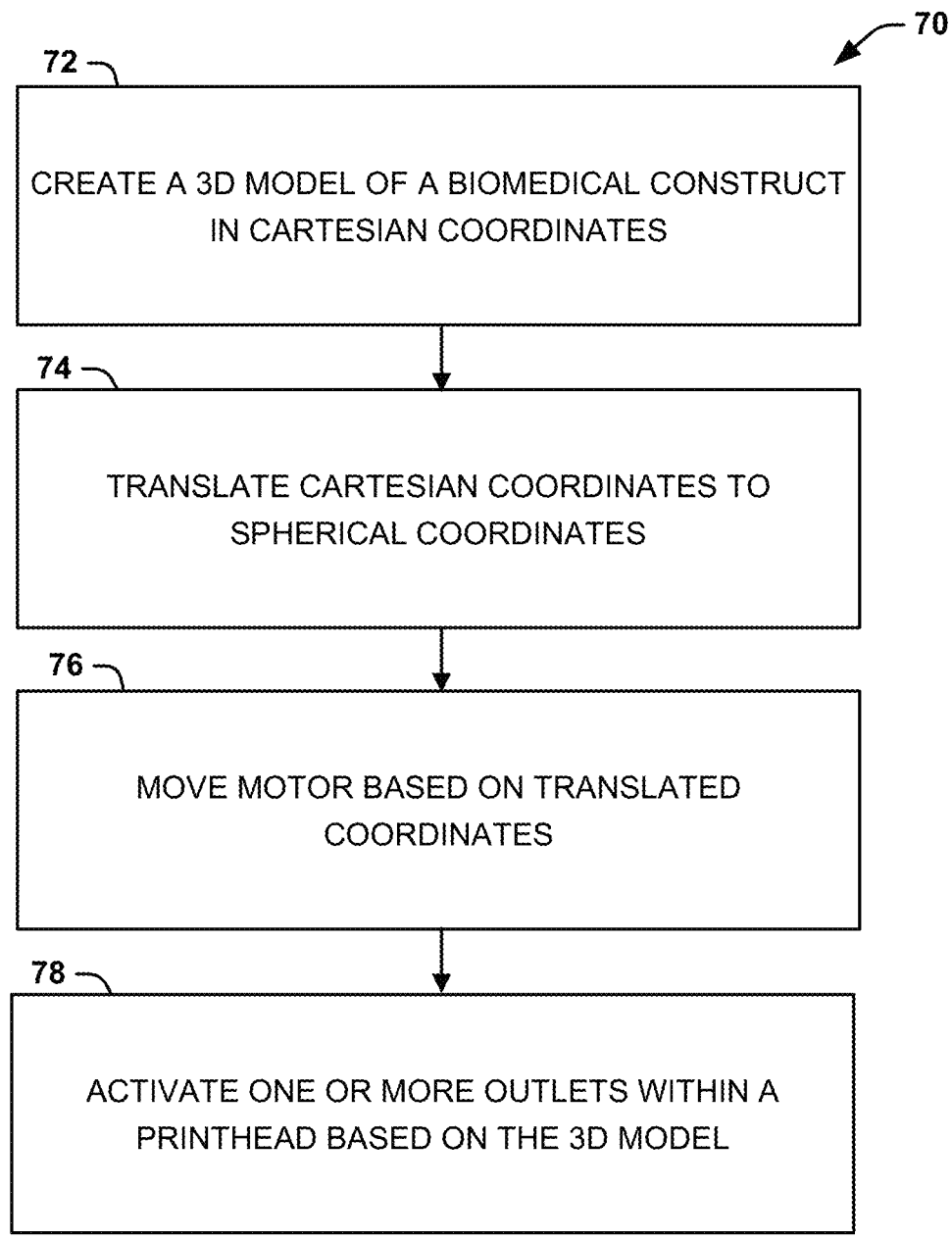
FIG. 7 is a process flow diagram of an example method for controlling the multi-material bioprinting according to the method of FIG. 6.

The methods 60 and 70 of FIGS. 6 and 7 are illustrated as a process flow diagram. For purposes of simplicity, the methods 60 and 70 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 60 and 70.

FIG. 6 illustrates a method 60 for multi-material bioprinting. For example, the method 60 can be executed by at least the printhead 12, the outlets 14, the reservoirs 16, and the controller 17 of FIG. 1. At 62, at least one outlet within the printhead of a bioprinter can be activated to print a bioink according to a bioprinting program. For example, the activation can include extruding the bioink from the activated outlet. The bioprinting program can be based on the model of the biomedical construct and created and/or enacted by the motor control 26 and the bioink control 27 in combination. The outlet can be activated based on an extrusion mechanism. The extrusion mechanism is a mechanical pressure change, a pneumatic pressure change, a thermal activation, and a piezoelectric activation, or the like.

At 64, a location of the printhead can be changed according to the bioprinting program. The location can be changed in at least one of a predefined movement in a rectangular (Cartesian) coordinate system and a spherical coordinate system. In some instances, the movement can be accomplished by one or more of the motors 19. However, in other instances, the movement is not of the printhead itself, but of a printing stage associated with the printhead. In still other instances, the movement is of both the printhead and the printing stage.

At 66, at least one other outlet of the plurality of outlets can be activated to print another bioink according to the bioprinting program. For example, the activation can include extruding the bioink from the at least one other activated outlet. The at least one other outlet can be activated based on an extrusion mechanism. The extrusion mechanism is a mechanical pressure change, a pneumatic pressure change, a thermal activation, and a piezoelectric activation, or the like. In some instances, the at least one other outlet can be activated based on a different level of the same extrusion mechanism as the outlet. However, in other instances, the at least one other outlet can be activated by the same level of the extrusion mechanism at the outlet. In still other instances, the at least one other outlet can be activated by an entirely different extrusion mechanism. At 68, at least one of the activated outlets can be deactivated to stop printing the associated bioink according to the bioprinting program.

Referring now to FIG. 7, illustrated is a method 70 for controlling the multi-material bioprinting. The method 70 can be executed by the controller 17 and/or the computing device 20. At 72, a 3D model of a biomedical construct can be created in Cartesian coordinates. For example, the 3D model can be created using a CAD program, like SOLID-WORKS®. At 74, the Cartesian coordinates can be translated to spherical coordinates. At 76, a motor can be moved based on the translated coordinates. For example, the motor can be associated with the printhead 12 and/or a housing 18 associated with the printhead. At 78, one or more outlets within the printhead can be activated based on the 3D model.

Experimental

The following example is shown for the purpose of illustration only and is not intended to limit the scope of the appended claims. This example illustrates the feasibility of bioprinter with a single printhead for multi-material bioprinting. The single printhead of this example includes multiple channels, each loaded with a unique bioink, which enables extremely rapid multi-material bioprinting at least one order of magnitude faster than any existing multi-nozzle platforms. Additionally, the single printhead design can be of a size, dimension, and stiffness to facilitate in vivo minimally invasive fabrication of the biomedical construct.

Methods

Chemicals and Materials

Alginate, methacrylic anhydride, and 2-hydroxy-4'-(2-hydroxyethoxy)-2-methylpropiophenone (photoinitiator, PI), sucrose, (3-trimethoxysily) propyl methacrylate (TMSPMA), polyethylene diacrylate (PEGDA), and calcium chloride dehydrate were purchased from Sigma-Aldrich (St Louis, Mo.). Nanoclay platelets (Cloisite 30b, i.e. nanosilicates) were obtained from Southern Clay Products (Gonzales, Tex.). The multiwalled carbon nanotubes (CNTs) (15±5 nm in diameter and 5-20 μmin length, 95% purity) were purchased from NanoLab (Waltham, Mass.).

Gelatin methacryloyl (GelMA) was synthesized according to a previously published protocol, at a high degree of methacrylation (81.4±0.4%). All reagents were used without further purification. The connectors for fabrication of the printheads were purchased from Instech Laboratories (Plymouth Meeting, Pa.). Cell analysis reagents including cell trackers BlueCMAC, GreenCMFDA, and CM-Dil, LIVE/DEAD kit, Alexa 488-phalloidin, and 4',6-diamidino-2-phenylindole (DAPI) were purchased from ThermoFisher Scientific (Waltham, Mass.). Food dyes were purchased from AmeriColor (Placentia, Calif.). All the antibodies were purchased from Abcam (Cambridge, Mass.). These chemicals and materials are a non-exclusive list of possible chemicals that can be used in connection with the bioprinter described herein.

Construction of the Single Printhead Bioprinter

Bioprinter Hardware

Figure 8:
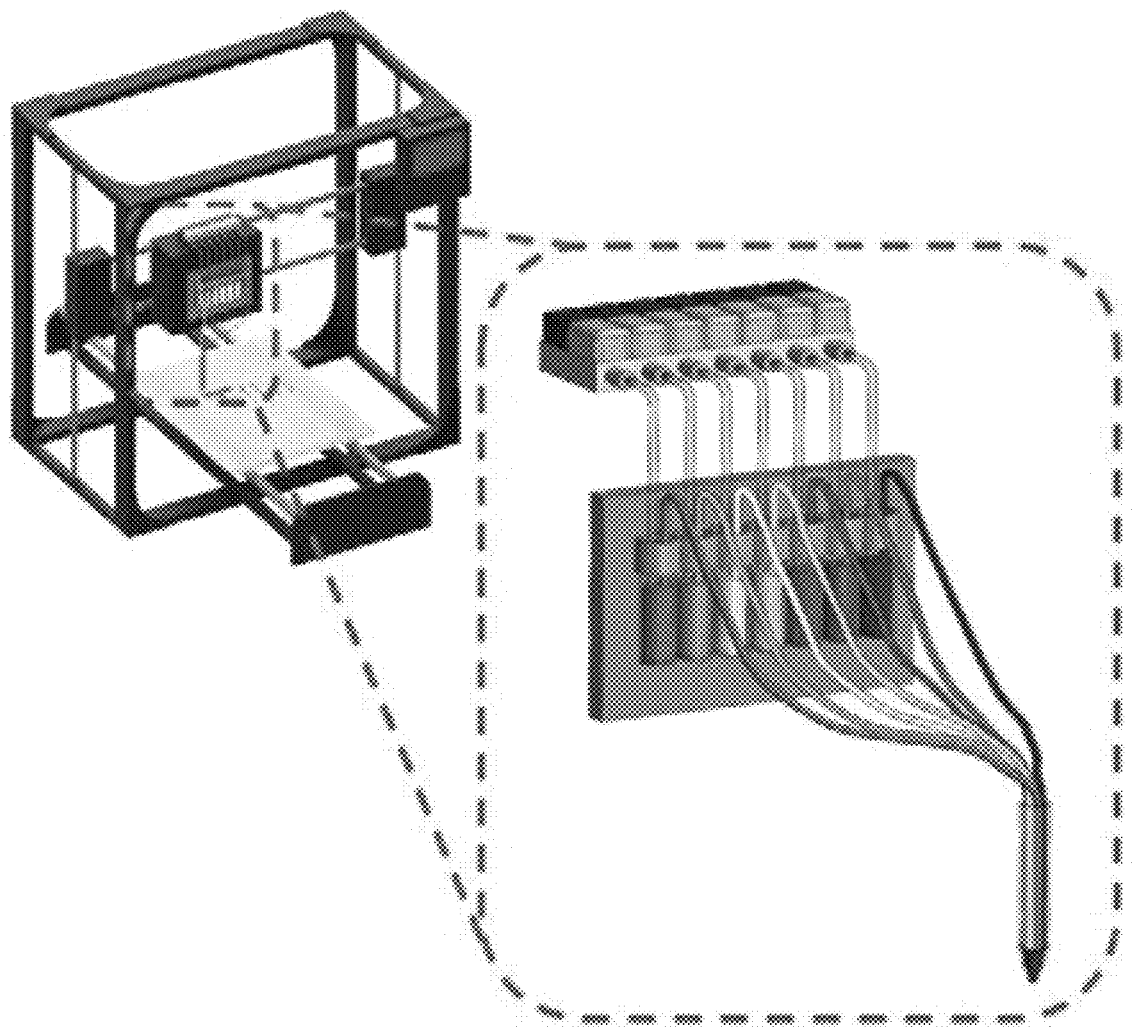
FIG. 8 is a schematic diagram showing an example design of a 7-channel printhead connected to reservoirs that are individually activated by programmable pneumatic valves.

'The 3D bioprinter was customized from an existing 3D printer (Lulzbot; Aleph Objects, Loveland, Colo.). The bioprinter consisted of an array of 7 valves/reservoirs and a Cartesian robotic stage. The dispensers were pneumatically driven and fed by compressed nitrogen (from 0 to 80 psi) through Tygon tubes (0.51 mm ID, 1.52 mm OD; Cole-Parmer, Vernon Hills, Ill.) connected to individual reservoirs (FIG. 8). The adjustment of nitrogen pressure and valve gating speed allowed the dispersion of various liquids with different viscosities. The temperature (between 35 and 40° C.) was monitored using the temperature sensor embedded the printer. The hardware was designed as detachable modules and was compatible with the original printer. This system further allowed increase of the number of the channels on demand, by simply extending the number of the digitally tunable valves. The single-nozzle extrusion printhead was obtained by pulling 7-barrel glass capillaries over flame and then tapering the head, thus providing a smooth transition from individual barrels to the final head.

Alternatively, printheads were also constructed by bundling metal connectors (ID 241 μm; 27G) in order to reach larger sizes of the printouts. The use of the printhead from the bundled metal connector was also more stable and less prone to breakage than the glass printheads. Single 27 G connectors were also used to test bioink printability.

Software Interface and Programming

The pneumatic valves for actuating the reservoirs were controlled from a relay board assembly that converted the commands of the program into electrical current and was compatible to the Arduino programming language. Marlin, an open source firmware, was used to program the Arduino-based RAM board. In addition, a general Gcode was written, which translates a previously designed model into movements in the X-Y-Z directions to operate the 3D Cartesian robotic stage along with coordinated actuation of desired pneumatic valves. The models were designed in SOLIDWORKS® (Concord, Mass.) and then converted to G-code by open-source Cura software (provided by Alpha Objects), which cuts the 3D model into slices with predetermined thickness and generates the G-code commands readable by the customized bioprinter. However, the 3D model can be custom made and cut without dependence on any pre-existing programs.

Bioink Characterization and Preparation

All solutions were measured by m/v [g m$^{-1}$] in concentrations, unless otherwise noted.

Rheology Measurement

The rheology of the bioinks was measured using a controlled stress rheometer (DHR-3, TA Instruments, New Castle, Del.) with a 40 mm diameter, 2° cone, and plate geometry. Rheology measurements for nanosilicate-based bioinks were conducted at room temperature at 37° C. for bioinks involving GelMA.

Nanosilicate Bioink

Nanosilicates of various concentrations (0-6%) were dissolved in distilled water. The optimum concentration of 5% was determined and used to demonstrate the capability of continuous multi-material bioprinting. Food dyes of different colors were added into the bioink when necessary.

Figure 9:
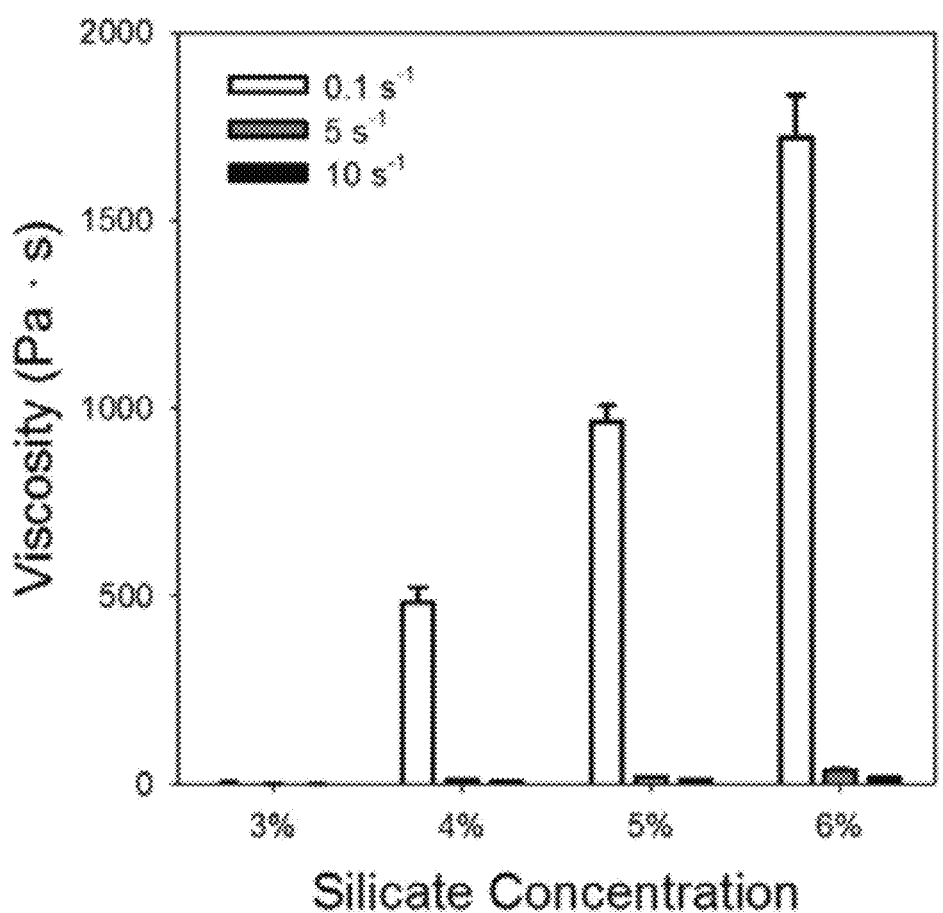
FIG. 9 is a plot showing the viscosity versus shear rate for bioinks containing different percentages of silicates at 0.1 $s^{-1}$, 5 $s^{-1}$, and 10 $s^{-1}$.

The viscosity of the nanosilicate bioinks at low shear rates significantly increased as the concentration of silicate was raised, reaching 1.1±0.1, 482.5±40.1, 965.0±40.7, and 1721.5±113.3 Pa·s at the shear rate of 0.1-1, for inks containing 3%, 4%, 5%, and 6% nanosilicates, respectively. It was further estimated that the shear rate experienced by the inks during the material extruding process would increase to approximately 5-10 s$^{-1}$, where the viscosity of the inks were all reduced to <50 Pa·s (FIG. 9) to facilitate the deposition of the materials. However, when the concentration of nanosilicates reached 6%, the pneumatic pressure required to drive the flow of the inks became exceedingly large; therefore, a bioink composition containing 5% silicate was chosen for subsequent characterization of the single printhead bioprinter to maintain the structural stability of the printed constructs.

Using the nanosilicate-based shear-thinning bioink, the effect of nozzle size, pneumatic pressure, and printhead movement speed on the properties of the resulting extruded microfibers were determined. As expected, the size of the printed microfibers could be controlled by the diameter of the nozzles. For example, microfibers with a diameter range of approximately 450 µm to 750 µm was attainable with nozzle sizes of 200-600 µm, when the pressure and printhead moving speed were constant at 55 psi and 200 mm min$^{-1}$, respectively.

Figure 10:
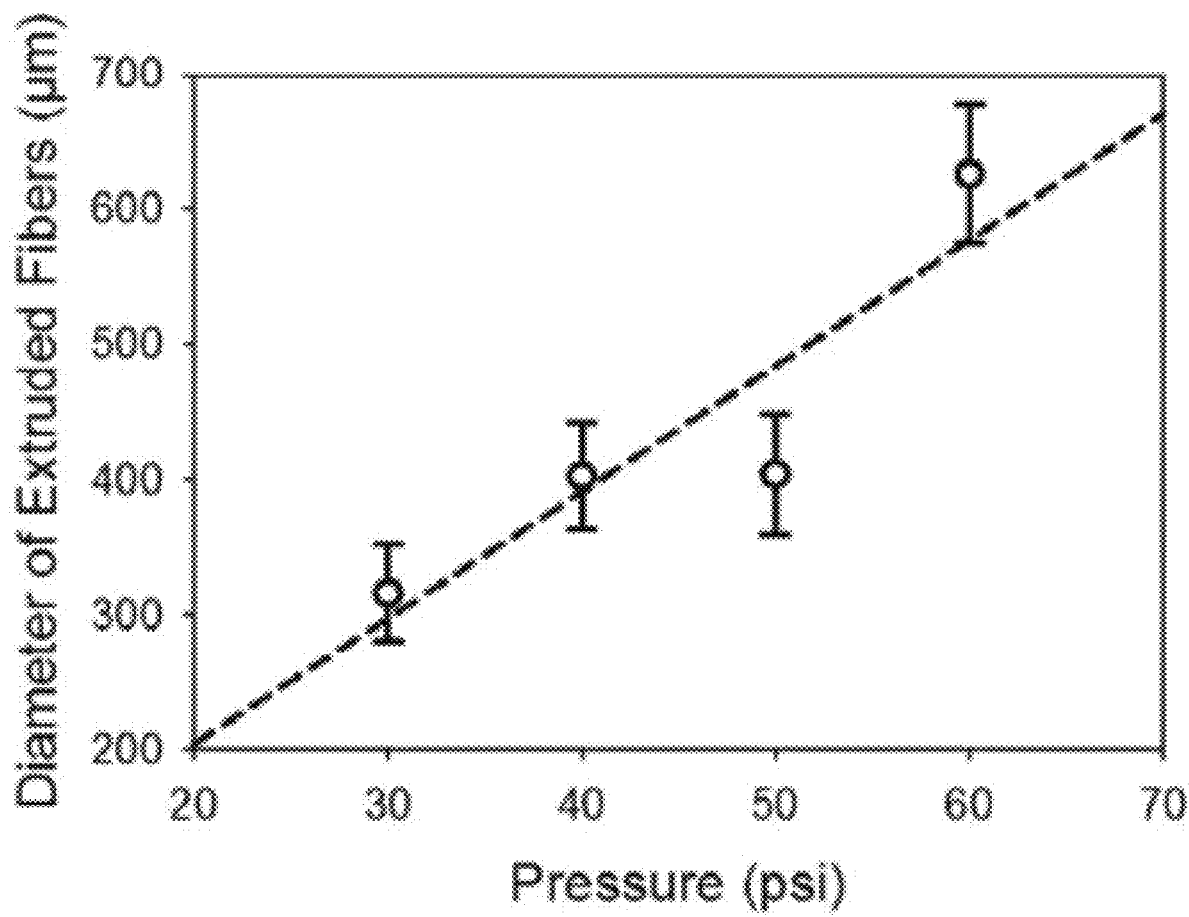
FIG. 10 is a plot showing that the diameter of extruded silicate-based microfibers increased with elevated pneumatic pressure at a constant printhead moving speed of 400 mm $min^{-1}$.
Figure 11:
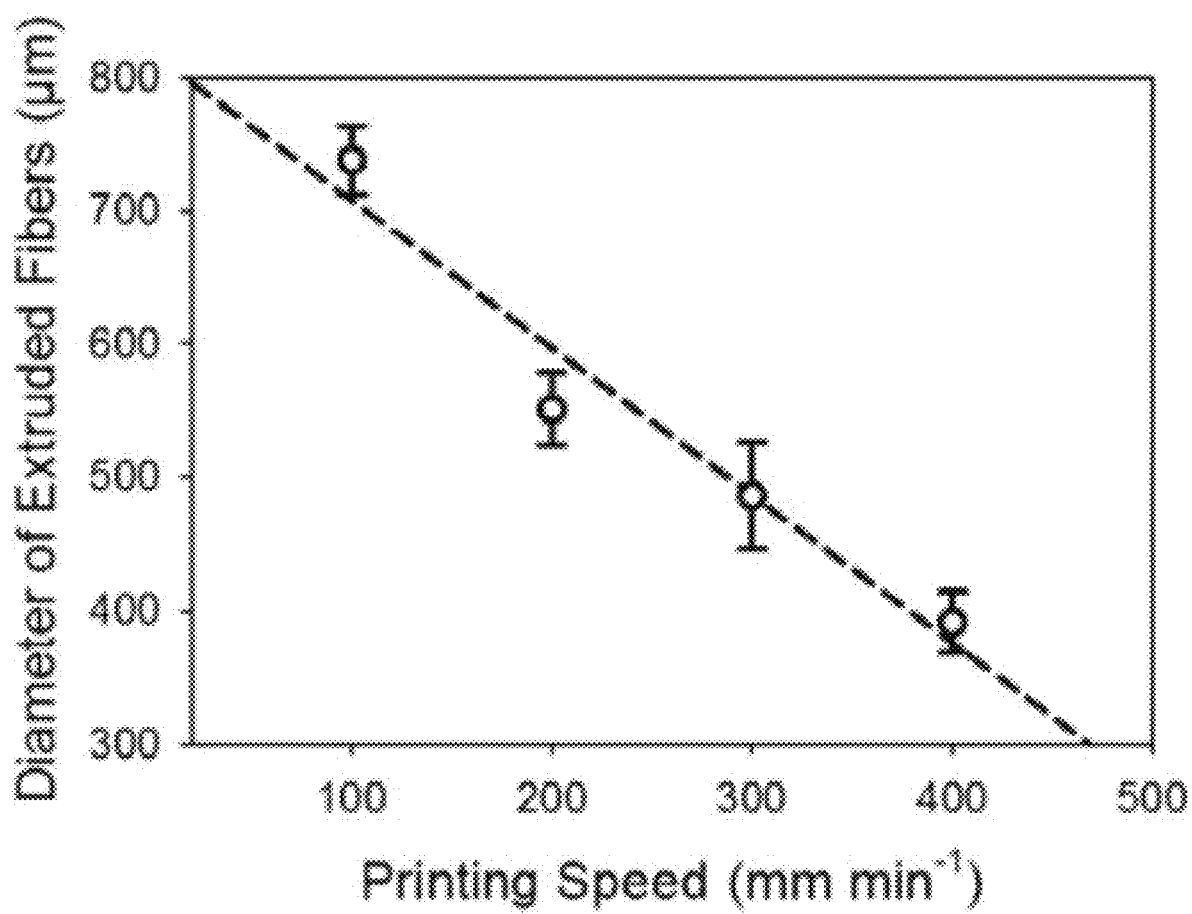
FIG. 11 is a plot showing that the diameter of extruded silicate-based microfibers decreased with a faster printhead speed at a constant pneumatic pressure of 50 psi.

The diameter of the deposited bioinks increased from 315.8±36.0 µm at 30 psi to 626.2±50.9 µm at 60 psi, when the speed of the printhead was fixed at 400 mm min$^{-1}$ (FIG. 10). On the contrary, the diameter decreased from 738.0±25.8 µm to 391.0±22.7 µm when the speed was elevated from 100 mm min$^{-1}$ to 400 mm min$^{-1}$ at a set pressure of 50 psi (FIG. 11). The flexibility in controlling the size of the printed microfibers by simply adjusting the pressure applied to the reservoir and moving speed of the printhead gave us a convenient choice of resolution for bioprinting different types of biomimetic constructs. A subsequent analysis of the printability of the bioink revealed that the printed constructs all maintained good stability, but the fidelity of the structures was compromised when the bioink extrusion became too slow or too fast compared to the moving speed of the printhead (a printability table was accordingly derived). Conditions that were considered printable were used in the subsequent experiments to illustrate the capability of the continuous multi-material bioprinter in the fabrication of 2D and 3D patterns.

GelMA/Alginate Bioink for Cell Encapsulation

The bioink used for the cell studies was prepared according to the following procedure. First, 1% PI and 2% alginate were separately dissolved in fetal bovine serum (FBS); the alginate solution was kept at room temperature overnight while the PI solution was incubated for 10 min at 80° C. to allow complete dissolution. Prior to the printing, the two solutions were then mixed to reach a final concentration of 1% alginate and 0.5% PI. Afterwards, 5% GelMA was added into the solution and incubated for 10 min at 37° C. for dissolution. Finally, the harvested cell pellet was mixed with the bioink and pipetted to homogenize the suspension.

Figure 12:
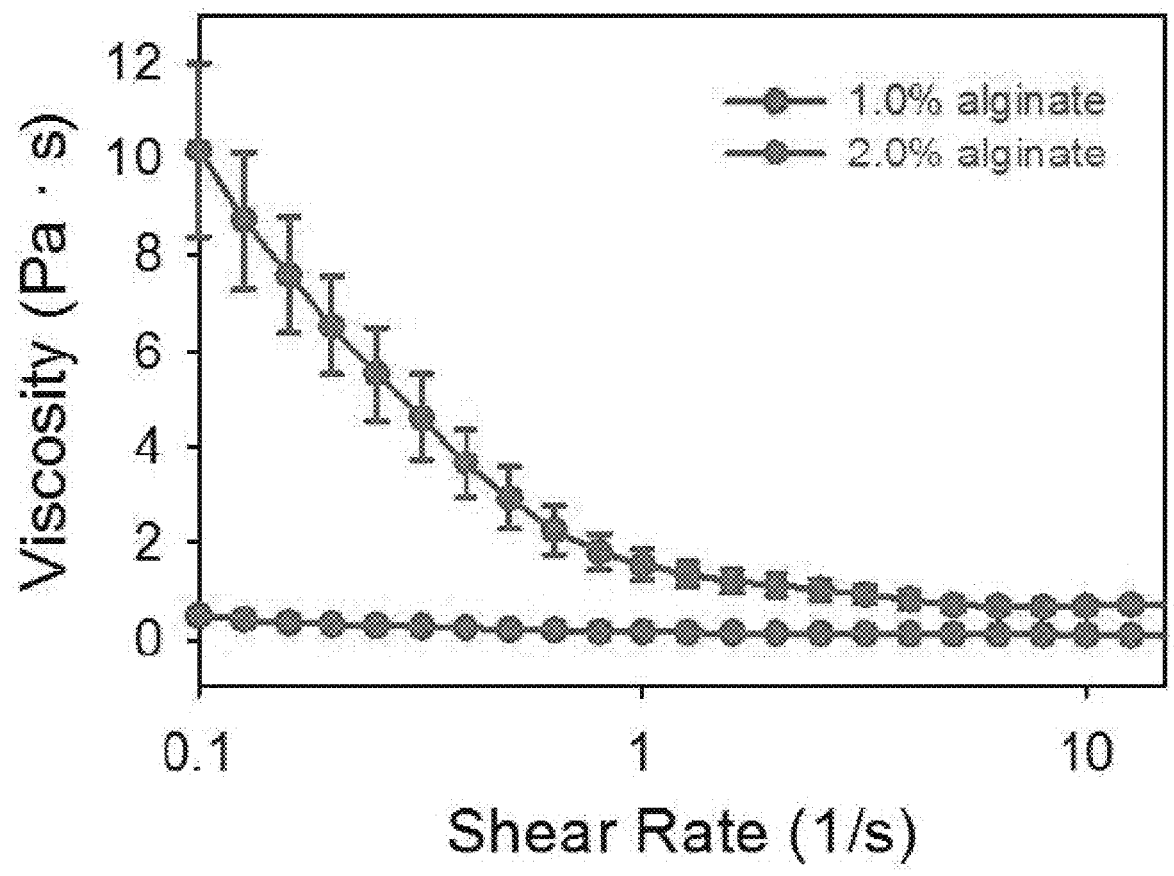
FIG. 12 is a plot of a rheology measurement of an alginate-5% GelMA bioink with the concentration of alginate altered from 1.0% to 2.0%.
Figure 13:
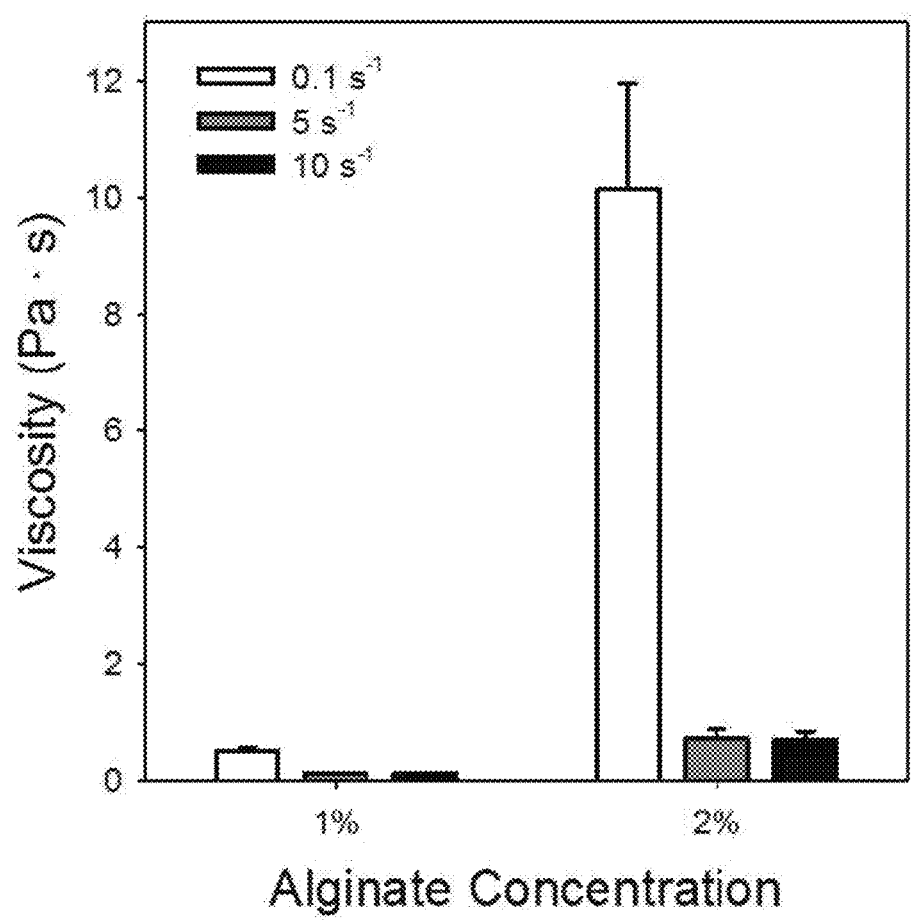
FIG. 13 is a plot showing the viscosity of the alginate-5% GelMA bioink with the concentration of alginate altered from 0.1% to 2.0% at shear rates of 0.1 $s^{-1}$, 5 $s^{-1}$, and 10 $s^{-1}$.

Similar to the silicate-based bioinks, the GelMA-alginate bioinks were also shear-thinning (FIGS. 12 and 13), facilitating easy extrusion of the materials during the printing process.

Figure 14:
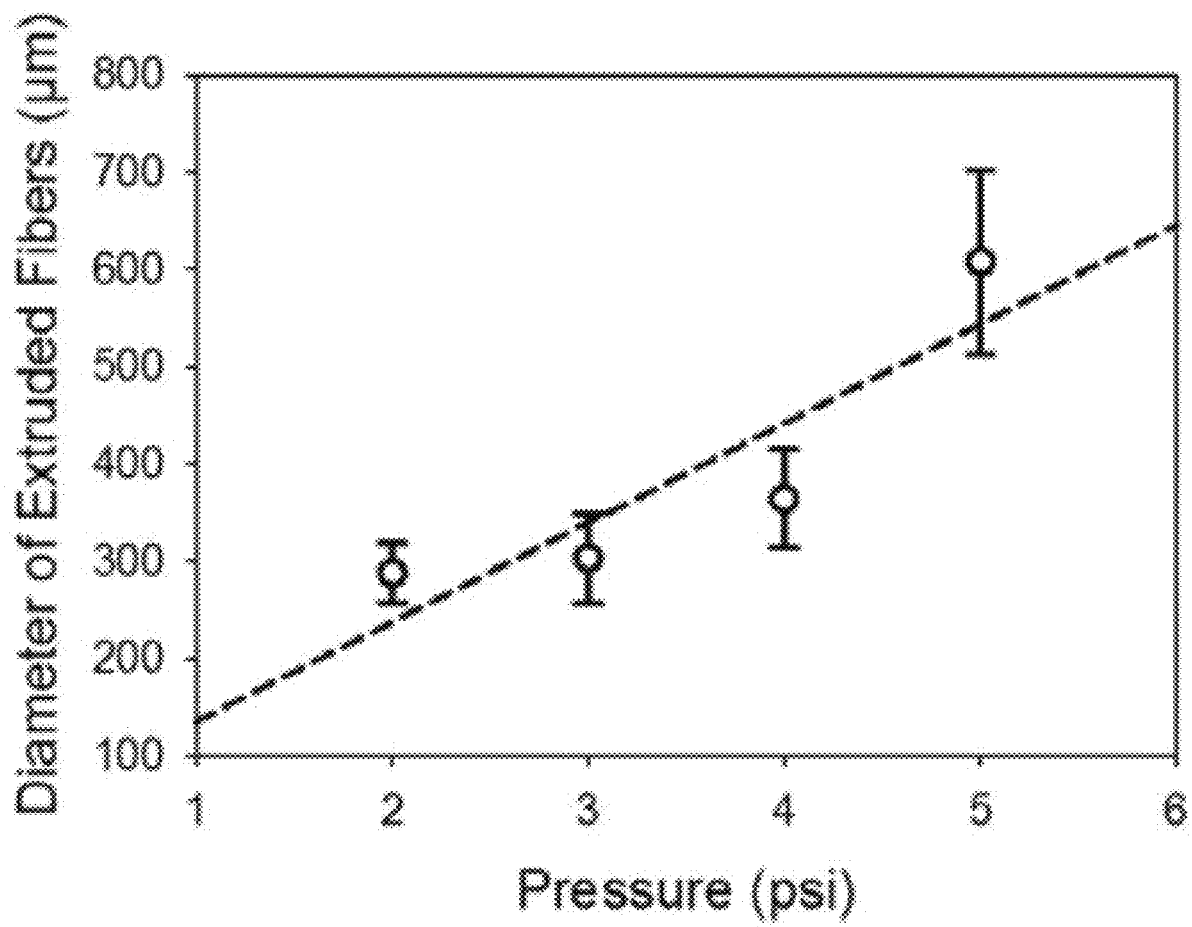
FIG. 14 is a plot showing that the diameter of extruded 5% GelMA/1% alginate microfibers increased with an elevated pneumatic pressure at a constant printhead moving speed of 400 mm $min^{-1}$.
Figure 15:
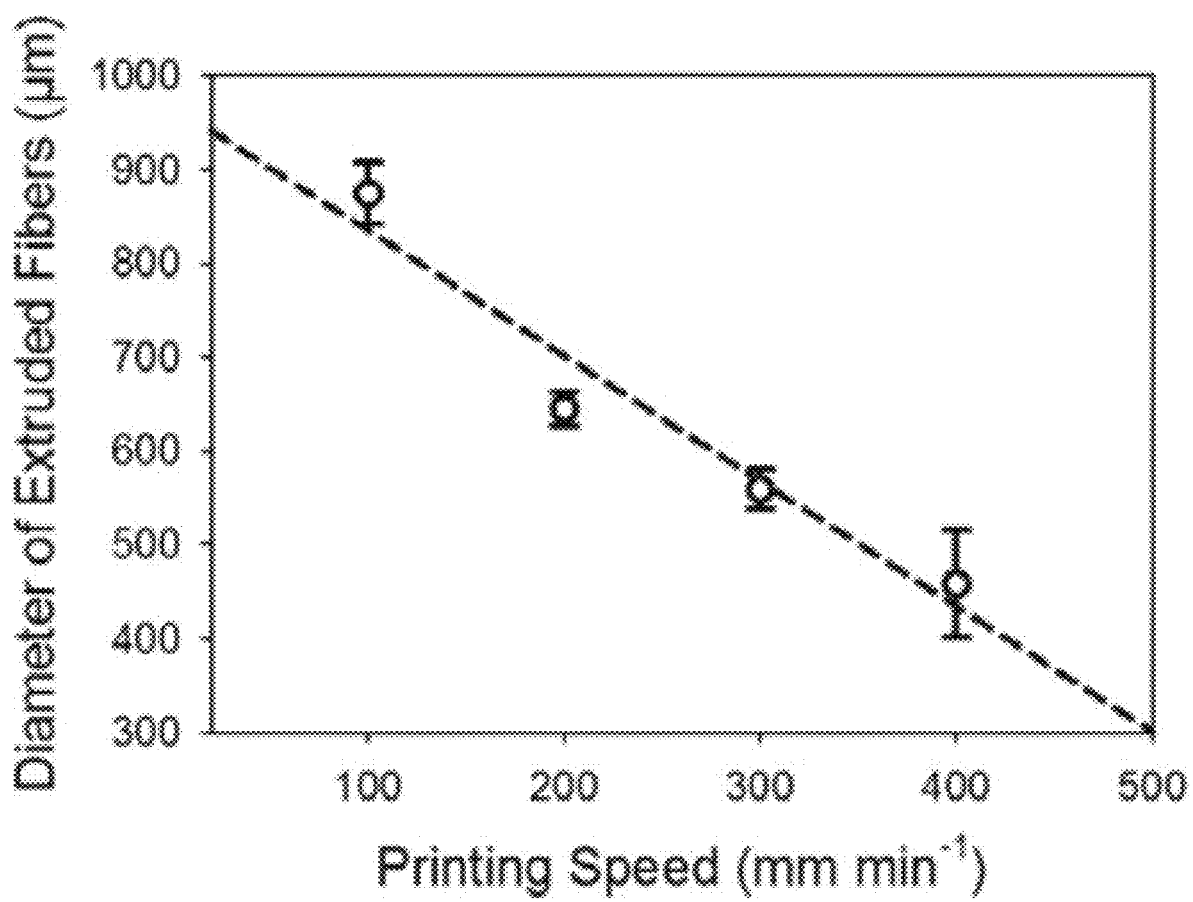
FIG. 15 is a plot showing that the diameter of extruded 5% GelMA/1% alginate microfibers with faster printhead moving speed at a constant pneumatic pressure of 3 psi.

The alginate concentrations of 1% and 2% were both used for subsequent experiments. The effects of pneumatic pressure and printhead moving speed on the parameters of extruded GelMA/1%-alginate microfibers were investigated. Similar to the nanosilicate-based inks, the diameter of the deposited bioinks increased when higher pressure was applied (FIG. 14), and it decreased upon elevation of the printing speed (FIG. 15), resulting in printed microfibers with a size range of approximately 150-450 µm under the conditions assessed. The printability of the GelMA/1%-alginate bioink also followed the same trend observed with the silicates; the fidelity of the structures was compromised when the bioink extrusion was overly slow or fast in relation to the moving speed of the printhead.

GelMA/Alginate/HAP Bioink

The bioink was prepared by mixing 5% GelMA, 2.67% alginate, 0.5% PI, and various concentrations of hydroxyapatite (HAp) (0, 0.00416, 0.00833, 0.0167, 0.0333, 0.0667, and 0.133 mg mL$^{-1}$). In a typical process, 0-0.4 mg mL$^{-1}$ of HAp nanoparticles were added to distilled water containing 2% alginate and ultrasonicated for 30 min before diluted into different concentrations to match the anticipated final concentrations mentioned above. At the same time, another solution was prepared containing 3% alginate, 0.75% PI, and 7.5% GelMA. Before bioprinting, both solutions were mixed at a ratio of 1:2 (HAp-alginate solution:alginate/GelMA/PI solution) and homogenized. Alizarin Red staining was performed according to standard protocols.

GelMA/Alginate/Sucrose/Anti-*Escherichia coli* (*E. coli*) Antibody Bioink

The bioink was prepared using 5% GelMA, 2% alginate, and various concentrations of anti-*E. coli* antigen (0.1-50 mg mL$^{-1}$) dissolved in distilled water containing 10% sucrose. The solution was kept in the incubator at 37° C. overnight, allowing the GelMA to dissolve completely. A total of 6 different final concentrations of the antibody were achieved: 6.25, 12.5, 25.0, 50.0, 100.0, and 200.0 µg mL$^{-1}$.

Alginate/CNT/DNA Bioink

The composite bioink consisting of multiwalled CNTs and alginate was prepared as follows: CNTs were added to 8 mg mL$^{-1}$ DNA solution and sonicated for 1 h in a water bath until a homogeneous solution was obtained. Subsequently, 3% alginate was mixed with the CNT/DNA solution to obtain final bioink containing 2% alginate and various concentrations of CNTs (1, 2, 3, 4, 5, 6 mg mL$^{-1}$).

Embedded Bioprinting

Bioink composed of either a pure 2% alginate aqueous solution or a combination of 20% PEGDA, 2% alginate, and 0.5% PI was used. The supporting hydrogel was prepared by adding 27% Pluronic F-127 (Sigma-Aldrich) to DI water containing 5% CaCl$_2$. The supporting hydrogel was incubated at 37° C. for 15 min prior to printing to reach optimal printing viscosity. After embedded printing a resting period of 30 min was left to allow the alginate to be crosslinked. In case where PEGDA was used the construct was crosslinked by exposure to UV light (850 mW cm$^{-2}$) for 30 s. Afterwards the Pluronic was liquefied at 4° C. for 10 min to retrieve the printed construct.

Mammalian Cell Studies

Cell Culture 5 different types of cells were used, including human dermal fibroblasts (HDFs, CRL-2522, ATCC, Manassas, Va.), HepG2 (HB-8065, ATCC), human umbilical vein endothelial cells (HUVECs, cAP-0001, Angio-Proteomie, Boston, Mass.), human mesenchymal stem cells (hMSCs, PT-2501, Lonza, Hopkinton, Mass.), and MC3T3-E1 preosteoblasts (CRL-2593, ATCC). All cells were cultured in their respective culture media as instructed. In brief, HDFs and HepG2s were cultured in Dulbecco's Modified Eagle Medium (DMEM) supplemented with 10 vol.% fetal bovine serum (FBS) and 1 vol.% penicillin/streptomycin (Pen/Strep) (all purchased from ThermoFisher Scientific); HUVECs were cultured in endothelial growth medium-2 supplemented with BulletKit (Lonza) and 1 vol.% Pen/Strep; hMSCs and MC3T3 were cultured in Modified Eagle Medium alpha (MEM-α, ThermoFisher Scientific) supplemented with 10 vol.% FBS and 1 vol.% Pen/Strep. The cells were maintained at 37° C. in a humidified 5% CO2 incubator, and passaged at 70% confluency.

Cell Bioprinting

The cells were homogeneously mixed with the desired bioinks immediately prior to the bioprinting process, at a density of approximately $3 \times 10^6$ cells $mL^{-1}$. The printed cell-laden bioinks were crosslinked to fix their structures using a UV source (OmniCure S2000, Excelitas Technologies, Waltham, Mass.) at a power density of 850 mW $cm^{-2}$, based on optimized conditions. The exposure time was 30 s to prevent any negative influence of UV exposure on the cells, while still allowing the bioinks to be sufficiently crosslinked. The cells were pre-labeled with cell trackers prior to bioprinting in the co-culture demonstration to microscopically differentiate the different cell populations, according to protocols provided by the manufacturer (ThermoFisher Scientific).

Characterization of Printed Constructs

The cell viability was analyzed by staining using a LIVE/DEAD assay accordingly to the manufacturer's instructions (ThermoFisher Scientific). In addition, the cells were stained using phalloidin/DAPI for f-actin/nuclei to visualize their morphologies when necessary. Fluorescence microscopy images were obtained using a Zeiss Axio Observer Microscope equipped with camera (Carl Zeiss, Thornwood, N.Y.).

Bacteria Studies

Green fluorescent *E. coli* bacteria (kindly donated from Tecnológico de Monterrey) were maintained in Lysogeny Broth Media (ThermoFisher) at a concentration of 0.5 mg $mL^{-1}$. The printed bioink squares containing different concentrations of anti-*E. coli* antibody were cured using UV light for 30 s. Subsequently, a suspension with approximately 0.5 mg bacteria (dry weight $mL^{-1}$) of a recombinant *E. coli* engineered to express green fluorescent protein (GFP) was incubated over the printed pattern at 37° C. for 30 min, and washed 3 times with PBS.

Statistics

Statistical analyses were conducted using unpaired t-tests with a sample size of at least 3 samples per group. Statistical significance was determined at $p<0.05$.

Results

Design and Characterization of the Rapid Continuous Multi-Material Bioprinter

Figure 16:
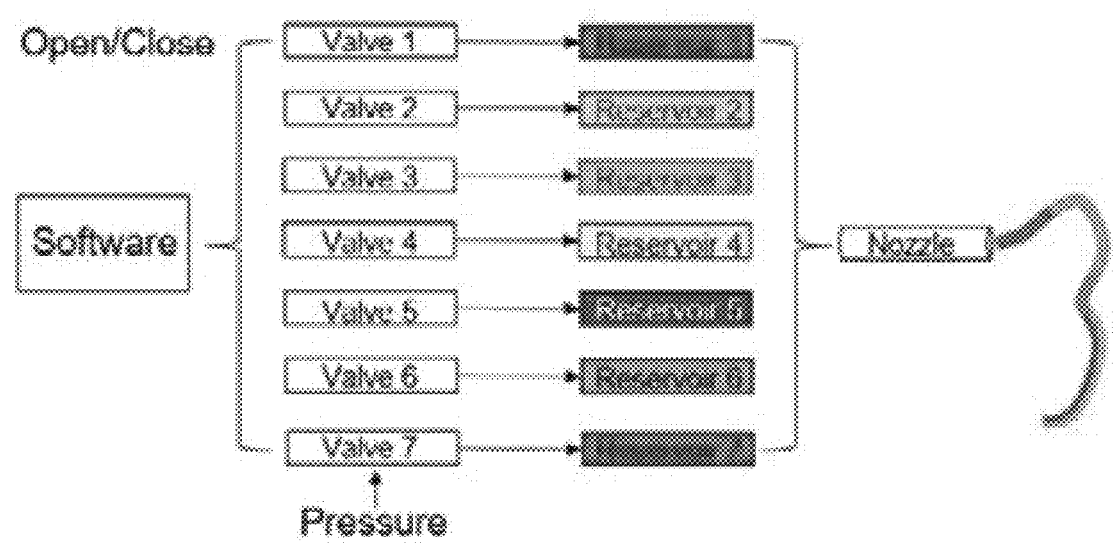
FIG. 16 is a schematic diagram showing the individualized actuation of different reservoirs according to the design of the bioprinter shown FIG. 8.

Unlike conventional multi-nozzle bioprinters, which typically require mechanical switching among physically separated nozzles to deposit multiple bioinks, the single printhead bioprinter described herein is able to continuously eject different types of inks in both individual and simultaneous modes. The single printhead bioprinter includes a Cartesian robotic stage and an array of bioink reservoirs routed to the single printhead containing 7 bundled channels (FIGS. 8 and 16). The dispensers are pneumatically driven and fed by compressed gas through valves. Digital tuning of the extrusion is achieved using a program integrated with the single-nozzle bioprinter to individually (or simultaneously) switch on/off desired valve(s) and command the dispensing patterns (FIG. 16). The controllers for both the valves and the motorized stage are programmed to synchronize the actuation of the valves and the movement of the stage. The adjustment of the pneumatic pressure and valve gating duration allows the dispersion of various bioinks with different viscosities. As such, the single-nozzle bioprinter can print up to 7 materials and rapidly switch among materials from different channels, without needing to physically change the nozzles.

Figure 17:
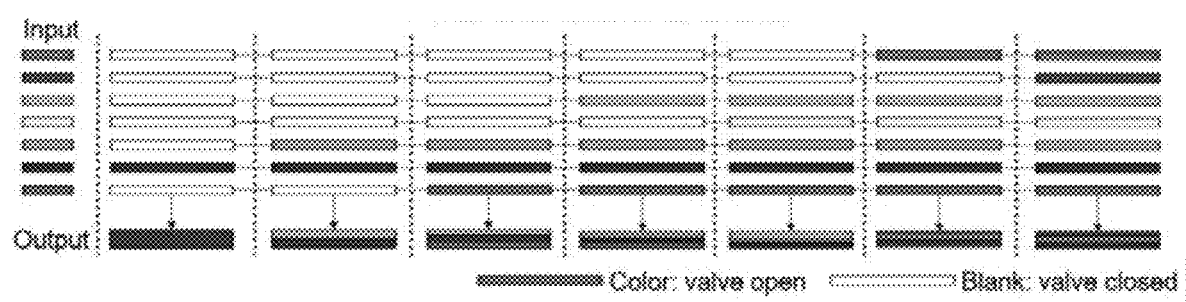
FIG. 17 is a schematic of a sample code for continuous bioprinting of a single serpentine microfiber by the bioprinter shown in FIG. 8.

For a typical multi-nozzle printer, the switch time between nozzles averages 4-20 s, while the single printhead bioprinter requires nearly no gap in such switching processes. As an example, the single printhead bioprinter was programmed to deposit bioinks dyed in 7 different colors with increasing numbers of colors after each switch (FIG. 17). The bioprinting process was continuous, and the printed microfibrous structure maintained its three-dimensionality consisting of an array of spatially well-defined bioinks. The 7 bioinks could also be individually deposited via a continuous printing process, where no noticeable switching delays were observed between adjacent materials.

In an experiment printing 15 lines, each composed of 7 bioinks for 2 layers (and thus 180 switches in total), while the single printhead bioprinter spent only 256 s for the entire printing process (at a speed of 400 mm $min^{-1}$), a conventional multi-nozzle printer will consume an additional time of 720-3600 s simply devoted to physical nozzle switching and result in a total printing time of 976-3856 s, if the patterns are deposited in the same manner. Therefore, the single-nozzle bioprinter could achieve a speed up to 15 times faster than those of the existing platforms. The advantage of the continuous multi-material printing system in terms of the biofabrication speed would become much more pronounced as the number of materials and the complexity of the printouts are increased. It should be noted that, the present system is readily expandable to as many bioinks as needed by simply increasing the number of pneumatically driven valves and reservoirs, thus affording the possibility to rapidly generate complex constructs while simplifying instrumentation.

Bioprinting of Planar and 3D Patterns

Using a shear-thinning bioink, formulated by a suspension of synthetic nanosilicates in water, a series of microfibrous 2D patterns were printed to demonstrate the capability of the single printhead bioprinter for continuous extrusion of multiple materials in well-defined manners. Each of the 7 bioinks could be continuously printed in equivalent lengths along the direction of the individual microfibers, with equal or incremental spacing between the adjacent lines. Alternatively, the spacing between the adjacent microfibers could be maintained constant while continuous segments within individual lines were printed with decreasing lengths, or both parameters might be altered simultaneously during the bioprinting process. An array of microfibers composed of increments of 1-7 materials along the direction of individual lines was also printed. Printing of these various patterns demonstrated the capability of the single printhead platform to continuously deposit any desired type and number of bioinks on demand. The different materials could also be printed in perpendicular directions, to achieve hierarchical architecture while still maintaining a clear separation of the deposited bioinks.

The printed multi-material microfibers could be designed to fuse into a single piece of structure when the spacing between the microfibers was reduced to match their width. The printed microfibers joined each other and formed a cohesive piece of monolayer slab containing 7 distinct but continuous segments along the direction of microfiber deposition. This ability to create fused larger-scale constructs allowed printing of more sophisticated patterns composed of multiple bioinks, which has hardly been possible using existing multi-printhead systems. The single printhead bioprinter has shown unparalleled power in overcoming this inability by depositing multiple types of materials in precisely programmed arrangements at much improved fabrication speed.

The single printhead bioprinter can produce complex 3D constructs. Simple cubes composed of 2 and 3 bioinks (and ring-shaped blocks containing 2, 3, and 4 bioinks were readily printed. Constructs containing all 7 bioinks could also be fabricated in different shapes, such as a pyramid, a three-layer stripe, and a ten-layer stripe. Sophisticated 3D patterns were designed and a set of structures were printed resembling human organs, including brain, lung, heart, liver, kidneys, pancreas, gastrointestinal system, and bladder. Each organ contained 1-3 deposition layers using 4-7 bioinks, according to the requirements of local structures, and each was individually printed. The bioprinting processes were rapid, and the transition among different bioinks was smooth. The printed organ-like constructs were stable, and the demarcation among adjacent materials was clear. The single printhead bioprinter was also compatible with the embedded bioprinting technique. Using a modified printhead with extended length, a free-form shape of PEGDA/alginate coils could be formed in a Pluronic hydrogel followed by photocrosslinking and retrieval after dissolution of the supporting matrix. Similarly, free-form alginate shapes composed of multiple bioinks, such as a dual-layer hollow tube and a DNA double helix, could be obtained with the single printhead bioprinter.

Extended Applications of Bioprinting for Cell-Laden Constructs, Biodevices, and Bioelectronics The single printhead bioprinter was shown to be able to generate hierarchical structures and patterns suitable for various applications in biomedicine, such as forming complex cell-laden organs, fabricating high-throughput point-of-care diagnosis devices, and depositing bioelectronic circuits.

Among the various photocrosslinkable hydrogels available, GelMA has been frequently used as a bioink due to its intrinsic cell adhesion moieties that promote cell spreading and functionality. Here, a mixture of GelMA and alginate was adopted as the bioink, where the alginate component was used to increase the viscosity to achieve a range of bioprinting conditions. The cell-laden bioinks were photo-crosslinked to fix their structures immediately after printing. A range of different patterns were designed, including the heart, kidney, and stripes with different width. It was clear that, multiple bioinks laden with cells pre-labeled with cell trackers were effectively deposited using the single printhead bioprinter with high reproducibility from the original designs. The printed structure possessed explicitly separated borders among different cell-laden bioinks. The resolution was determined to be approximately 100-200 µm, as indicated from the printed stripe patterns with a range of widths.

A pattern of vascularized tissue was printed, where four sectors of bioinks laden with HDFs, human hepatocellular cells (HepG2), hMSCs, and no cells, respectively, were deposited at the base, followed by integration of a pattern on top that mimicked the vasculature encapsulating HUVECs. The fluorescence micrographs obtained from different locations clearly revealed successful bioprinting of the desired (cell-laden) bioinks as programmed, which is essential for the fabrication of complex tissues containing hierarchical assembly of multiple cell types. The cell viability assays, determined immediately and at 1 and 7 days post bioprinting, indicated that all cell types maintained sufficient viability under the UV crosslinking conditions adopted. The cells well spread over a course of 7 days in culture, indicating the bioactivity provided by the GelMA component of the bioink. The printed vascularized tissue constructs were further shown to exhibit increased cell proliferation over a period of 13 days analyzed.

In addition, the single printhead bioprinter was used to generate gradient structures to mimic those occurring in natural tissues, such as the bone. For example, a ring-like structure featuring an inward-out gradient in the concentration of HAp was created. Alizarin Red staining and quantification of the staining intensities further confirmed the presence of this same type of gradient in HAp contents. Importantly, the shape of the printed constructs containing bioinks with different concentrations of HAp could be arbitrarily controlled to form any desired localized gradients as well as continuous or discrete patterns, as illustrated by the capability to print a bone-shaped hydrogel block. The Alizarin Red staining indicated that different bioinks containing a range of HAp concentrations were printed across the entire structure, where the same materials (#4 and 5, #6 and 7) printed at discrete locations showed similar staining intensity, revealing reproducible deposition of the bioinks as programmed.

The printed constructs featuring gradients of inorganic nanoparticles also demonstrated varying bioactivities. Differential attachment and proliferation of MC3T3 preosteoblasts seeded on top of the printed structure containing a gradient of HAp, were observed after 1 and 3 days of culture. The cell seeding efficiency and proliferation were promoted with increasing concentration of HAp. A similar trend in cell behaviors was observed when the preosteoblasts were seeded on printed hydrogels containing a gradient of nanosilicates based on the osteoinductive property of these nanoparticles. This excellent freedom in reliable and smooth switching among selected bioinks during the bioprinting process is critical in recapitulating tissue- and organ-level biomimetic properties, especially when sophisticated structures and/or complex compositions are involved.

The capacity of single printhead bioprinting platform could benefit the generation of point-of-care devices as well. Diagnostics plays a significant role in health care, by providing appropriate and timely care to patients, ensuring safe blood banking, and supplying crucial surveillance data for both emergency public health interventions and long-term public health strategies. Often, the most preferred point-of-care diagnostic devices are those capable of operating in a high-throughput manner, featuring an array of measurement units capable of detecting different markers/pathogens of interest. Based on this requirement, a proof-of-concept demonstration was provided by loading the single printhead bioprinter with bioinks containing a range of concentrations of antibody against *E. coli*, and printing 9 squares each with bioinks dispensed from a random reservoir. This device was incubated within a suspension of *E. coli* for 30 min, followed by rinsing with phosphate buffered saline (PBS) prior to microscopy observation. This device, containing a multitude of subunits with different concentrations of antibodies, successfully captured corresponding densities of the bacteria on the surfaces of the detection blocks. The number of unit blocks may be expanded to derive high-throughput point-of-care devices that are capable of simultaneously diagnosing multiple species of pathogens or types of biomarkers on demand.

Significant interest in bioelectronics is also emerging in biomedicine. A wide range of applications of electronics devices is possible in various fields, including epidermal sensors, soft contact lenses, neurointerfaces, implantable medical devices, and bioactuators. Bioprinting has been increasingly recognized as an excellent technique for depositing conductive bioinks for direct fabrication of bioelectronics, given its convenience, robustness, and cost effectiveness.

While many strategies have been developed for printing conductive bioinks, these have been mostly limited by single-ink deposition, which precluded the possibility for the production of complex electronic circuits. Taking advantage of the single printhead bioprinting platform, a continuous circuit was printed featuring conductive alginate/DNA/CNT bioinks with 1-6 mg mL$^{-1}$ CNTs in parallel. The printed circuit was completed by attaching a power source (coin battery, 3V) and 6 miniature green LEDs, which upon connection, exhibited a clear gradient in their luminescence intensity. The differential luminescence of the LEDs was attributed to the series of resistances (0.17-3.37 Ωmm$^{-1}$) that the conductive bioinks produced and therefore the difference in the current generated in each parallel unit.

From the above description, those skilled in the art will perceive improvements, changes and modifications. Such improvements, changes and modifications are within the skill of one in the art and are intended to be covered by the appended claims.

What is claimed is:

1. A multi-material bioprinter comprising:
   a housing comprising a biocompatible portion including a single printhead for in vivo bioprinting, wherein the single printhead comprises a motorized stage configured to move the single printhead; and
   a plurality of reservoirs separate from the housing, each reservoir housing a different bioink for bioprinting and connected to the single printhead,
   wherein the single printhead includes a plurality of outlets, each of the plurality of outlets is linked to one of the plurality of reservoirs by a valve, wherein each of the valves is configured to open when a respective outlet is activated by an extrusion mechanism with a different property, such that each of the outlets is independently activated to release a respective bioink from each of the plurality of outlets of the single printhead, wherein at least two of the plurality of outlets are able to release respective bioinks simultaneously, wherein each of the extrusion mechanisms is synchronized respectively with each of the valves and movement of the motorized stage to rapidly switch among materials from the plurality of reservoirs.

2. The multi-material bioprinter of claim 1, wherein the housing is within a handheld device or a robotically controlled device.

3. The multi-material bioprinter of claim 1, wherein the housing is adapted as at least one of a catheter device, a needle device, an endoscopy device, and an orthoscopy device.

4. The multi-material bioprinter of claim 1, wherein the biocompatible portion of the housing comprises a stiffness that is tunable for different applications.

5. . The multi-material bioprinter of claim 1 further comprising a controller comprising:
   at least one mechanism to control assembly and adhesion of printed patterns;
   a memory storing instructions and a model design for the printed pattern; and
   a processor to execute the instructions to:
      regulate activation of a predefined pattern of the plurality of outlets for a predefined amount of time to create the printed pattern,
      wherein the predefined pattern of the plurality of outlets is predefined based on the model design.

6. The multi-material bioprinter of claim 5, wherein the processor of the controller further executes the instructions to control movement of the single printhead according to the model design.

7. The multi-material bioprinter of claim 6, wherein the movement is defined in at least one of a Cartesian coordinate system or a spherical coordinate system.

8. The multi-material bioprinter of claim 5, wherein the model design corresponds to a three-dimensional software model.

9. The multi-material bioprinter of claim 1, wherein the extrusion mechanism comprises at least one of a mechanical pressure change, a pneumatic pressure change, a thermal activation, and a piezoelectric activation.

10. The multi-material bioprinter of claim 5, wherein the at least one mechanism to control assembly and adhesion of printed patterns comprises at least one motor.

11. The multi-material bioprinter of claim 1, wherein each of the valves are opened and/or shut to control a speed and/or a thickness of the bioink release.

* * * * *